United States Patent
Wu et al.

(10) Patent No.: US 9,836,121 B2
(45) Date of Patent: Dec. 5, 2017

(54) EYE-WIDTH DETECTOR, MEMORY STORAGE DEVICE AND EYE-WIDTH DETECTION METHOD OF DATA SIGNAL

(71) Applicant: PHISON ELECTRONICS CORP., Miaoli (TW)

(72) Inventors: Jen-Chu Wu, New Taipei (TW); Wei-Yung Chen, Hsinchu County (TW); Yu-An Chen, Taichung (TW)

(73) Assignee: PHISON ELECTRONICS CORP., Miaoli (TW)

( * ) Notice: Subject to any disclaimer, the term of this patent is extended or adjusted under 35 U.S.C. 154(b) by 224 days.

(21) Appl. No.: 14/856,563

(22) Filed: Sep. 17, 2015

(65) Prior Publication Data

US 2017/0031436 A1    Feb. 2, 2017

(30) Foreign Application Priority Data

Jul. 28, 2015 (TW) .............................. 104124444 A

(51) Int. Cl.
*G06F 3/01* (2006.01)
*A61B 3/11* (2006.01)

(52) U.S. Cl.
CPC ................ *G06F 3/013* (2013.01); *A61B 3/11* (2013.01)

(58) Field of Classification Search
CPC .. G06F 3/013; A61B 3/00; A61B 3/11; G02B 7/12
See application file for complete search history.

(56) References Cited

U.S. PATENT DOCUMENTS

| | | | | |
|---|---|---|---|---|
| 7,400,181 B2 * | 7/2008 | Metz | ..................... | H03L 7/0812 327/149 |
| 8,923,463 B1 * | 12/2014 | Jenkins | ................. | H04L 7/0334 375/355 |
| 8,934,594 B1 * | 1/2015 | Malhotra | ............ | H04L 27/2338 375/355 |
| 9,112,655 B1 * | 8/2015 | Hoang | ................... | H03L 7/0807 |
| 9,467,314 B1 * | 10/2016 | Wei | ........................... | H04L 7/00 |
| 9,673,966 B2 * | 6/2017 | Hammad | .............. | H04L 7/0054 |
| 2005/0108600 A1 * | 5/2005 | Arguelles | ......... | G01R 31/31715 714/701 |
| 2005/0259774 A1 * | 11/2005 | Garlepp | .................... | H04L 1/20 375/355 |
| 2013/0272358 A1 * | 10/2013 | Chen | ....................... | H04L 1/205 375/224 |
| 2014/0092951 A1 * | 4/2014 | Bhagavathula | ....... | H04L 7/0066 375/229 |

* cited by examiner

*Primary Examiner* — Kenneth Lam
(74) *Attorney, Agent, or Firm* — JCIPRNET

(57) ABSTRACT

An eye-width detector, a memory storage device and an eye-width detection method of data signal are provided. The eye-width detector includes a phase interpolator, a calibration circuit and an eye-width detection circuit. The phase interpolator receives a first clock signal and a phase control signal and output a second clock signal. The calibration circuit receives the first clock signal and the second clock signal and output a first control signal. The eye-width detection circuit receive the data signal, the first clock signal and the second clock signal and generate a first sampling value and a second sampling value. If the first sampling value and the second sampling value do not match a first condition, the eye-width detection circuit outputs a second control signal; otherwise, outputs eye-width information of the data signal. Accordingly, the efficiency of the eye-width detection may be improved.

35 Claims, 9 Drawing Sheets

EYE-WIDTH DETECTOR, MEMORY STORAGE DEVICE AND EYE-WIDTH DETECTION METHOD OF DATA SIGNAL

CROSS-REFERENCE TO RELATED APPLICATION

This application claims the priority benefit of Taiwan application serial no. 104124444, filed on Jul. 28, 2015. The entirety of the above-mentioned patent application is hereby incorporated by reference herein and made a part of this specification.

BACKGROUND

Technical Field

The disclosure relates to an eye-width detection technology, and more particularly, to an eye-width detector, a memory storage device and an eye-width detection method of data signal.

Description of Related Art

With advancements in data transmission speed, performance demands of receivers capable of improving data receiving capability at the receiving end have also become stronger. For example, an adaptive equalizer is widely used in the receivers of the wired transmission. In general, the adaptive equalizer is disposed with one equalizer and one eye-width detector. The eye-width detector detects an eye-width of a data signal processed by the equalizer. The detected eye-width may be used by the adaptive equalizer. For example, the adaptive equalizer may adjust parameters of the equalizer according to the detected eye-width. According to the adjusted parameters of the equalizer, the equalizer may gradually improve a signal quality of the data signal outputted by the equalizer. For example, if the eye-width of the data signal outputted by the equalizer is wider, a sampling correctness of the data signal may be higher.

The common eye-width detector performs a matching test on the currently-processing data signal by using a large amount of eye-width data until a set of the eye-width data matched to the currently-processing data signal is found. However, this method of detecting the eye-width by performing a blind test which uses the large amount of data is not suitable for the receiver with higher data transmission speed.

Nothing herein should be construed as an admission of knowledge in the prior art of any portion of the present disclosure. Furthermore, citation or identification of any document in this application is not an admission that such document is available as prior art to the present disclosure, or that any reference forms a part of the common general knowledge in the art.

SUMMARY

The disclosure is directed to an eye-width detector, a memory storage device and an eye-width detection method of data signal, which are capable of improving an efficiency of the eye-wide detection.

An exemplary embodiment of the disclosure provides an eye-width detector, which includes a phase interpolator, a calibration circuit, an eye-width detection circuit and a multiplexer. The phase interpolator is configured to receive a first clock signal and a phase control signal and output a second clock signal. The calibration circuit is coupled to the phase interpolator. The calibration circuit is configured to receive the first clock signal and the second clock signal and output a first control signal. The eye-width detection circuit is coupled to the phase interpolator and the calibration circuit. The eye-width detection circuit is configured to receive a data signal, the first clock signal and the second clock signal and generate a first sampling value and a second sampling value. If the first sampling value and the second sampling value do not match a first condition, the eye-width detection circuit is further configured to output a second control signal. If the first sampling value and the second sampling value match the first condition, the eye-width detection circuit is further configured to output eye-width information of the data signal. The multiplexer is coupled to the phase interpolator, the calibration circuit and the eye-width detection circuit. The multiplexer is configured to receive the first control signal and the second control signal and output the phase control signal in response to a selection signal.

Another exemplary embodiment of the disclosure provides a memory storage device, which includes a connection interface unit, a rewritable non-volatile memory module and a memory control circuit unit. The connection interface unit is configured to couple to a host system. The memory control circuit unit is coupled to the connection interface unit and the rewritable non-volatile memory module. The connection interface unit includes an eye-width detector. The eye-width detector includes a phase interpolator, a calibration circuit, an eye-width detection circuit and a multiplexer. The phase interpolator is configured to receive a first clock signal and a phase control signal and output a second clock signal. The calibration circuit is coupled to the phase interpolator. The calibration circuit is configured to receive the first clock signal and the second clock signal and output a first control signal. The eye-width detection circuit is coupled to the phase interpolator and the calibration circuit. The eye-width detection circuit is configured to receive a data signal, the first clock signal and the second clock signal and generate a first sampling value and a second sampling value. If the first sampling value and the second sampling value do not match a first condition, the eye-width detection circuit is further configured to output a second control signal. If the first sampling value and the second sampling value match the first condition, the eye-width detection circuit is further configured to output eye-width information of the data signal. The multiplexer is coupled to the phase interpolator, the calibration circuit and the eye-width detection circuit. The multiplexer is configured to receive the first control signal and the second control signal and output the phase control signal in response to a selection signal.

Another exemplary embodiment of the disclosure provides an eye-width detection method of data signal, which includes: receiving a first clock signal and a phase control signal and outputting a second clock signal; receiving the first clock signal and the second clock signal and outputting a first control signal; receiving a data signal, the first clock signal and the second clock signal and generating a first sampling value and a second sampling value; outputting a second control signal if the first sampling value and the second sampling value do not match a first condition; outputting eye-width information of the data signal if the first sampling value and the second sampling value match the first condition; and receiving the first control signal and the second control signal and outputting the phase control signal in response to a selection signal.

Based on the above, the phase interpolator receives the first clock signal and the phase control signal and outputs the second clock signal. The calibration circuit receives the first clock signal and the second clock signal and outputs the first control signal. The eye-width detection circuit receives the data signal, the first clock signal and the second clock signal and generates the first sampling value and the second sampling value. If the first sampling value and the second sampling value match the first condition, the eye-width detection circuit outputs the eye-width information of the data signal. If the first sampling value and the second sampling value do not match the first condition, the eye-width detection circuit outputs a second control signal. In addition, the multiplexer receives the first control signal and the second control signal and outputs the phase control signal in response to the selection signal. Accordingly, the efficiency of the eye-width detection may be improved.

To make the above features and advantages of the present disclosure more comprehensible, several embodiments accompanied with drawings are described in detail as follows.

It should be understood, however, that this Summary may not contain all of the aspects and embodiments of the present disclosure, is not meant to be limiting or restrictive in any manner, and that the disclosure as disclosed herein is and will be understood by those of ordinary skill in the art to encompass obvious improvements and modifications thereto.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
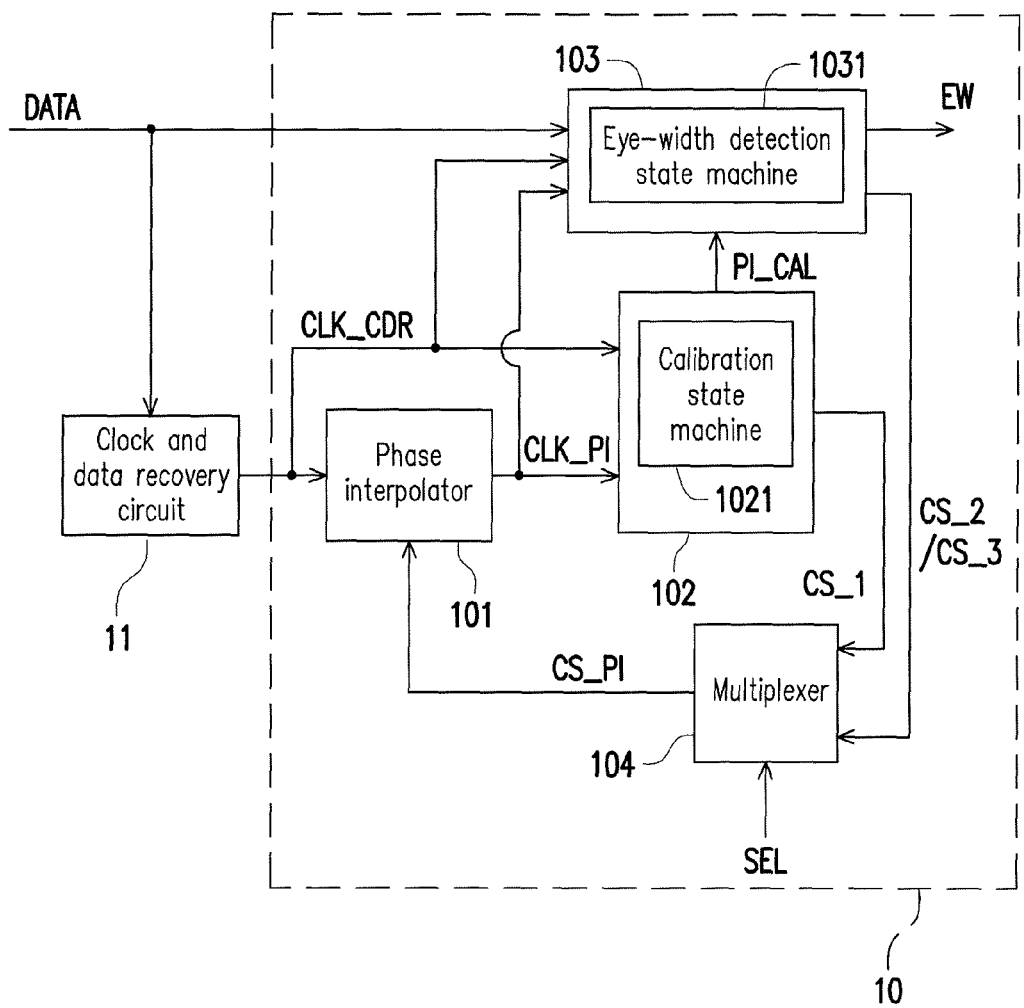
FIG. 1 is a schematic diagram illustrating an eye-width detector according to an exemplary embodiment of the disclosure.

Reference will now be made in detail to the present preferred embodiments of the disclosure, examples of which are illustrated in the accompanying drawings. Wherever possible, the same reference numbers are used in the drawings and the description to refer to the same or like parts.

Embodiments of the present disclosure may comprise any one or more of the novel features described herein, including in the Detailed Description, and/or shown in the drawings. As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" may be used interchangeably herein.

Embodiments are provided below to describe the present disclosure in detail, though the present disclosure is not limited to the provided embodiments, and the provided embodiments may be suitably combined. The term "coupling/coupled" used in this specification (including claims) may refer to any direct or indirect connection means. For example, "a first device is coupled to a second device" should be interpreted as "the first device is directly connected to the second device" or "the first device is indirectly connected to the second device through other devices or connection means." In addition, the term "signal" may mean a current, a voltage, a charge, a temperature, data or any one or multiple signals.

FIG. 1 is a schematic diagram illustrating an eye-width detector according to an exemplary embodiment of the disclosure.

Referring to FIG. 1, an eye-width detector 10 includes a phase interpolator 101, a calibration circuit 102, an eye-width detection circuit 103 and a multiplexer 104.

The phase interpolator 101 is configured to receive a clock signal CLK_CDR and a control signal CS_PI and output a clock signal CLK_PI.

The calibration circuit 102 is coupled to the phase interpolator 101. The calibration circuit 102 is configured to receive the clock signal CLK_CDR and the clock signal CLK_PI and output a control signal CS_1. The control signal CS_1 is configured to make a clock frequency of the clock signal CLK_PI to be consistent with a clock frequency of the clock signal CLK_CDR.

The eye-width detection circuit 103 is coupled to the phase interpolator 101 and the calibration circuit 102. The eye-width detection circuit 103 is configured to receive a data signal DATA, the clock signal CLK_CDR and the clock signal CLK_PI and generate a sampling signal pair. The sampling signal pair includes a first sampling value and a second sampling value. The eye-width detection circuit 103 determines whether the generated first sampling value and the generated second sampling value (i.e., the generated sampling signal pair) match one specific condition (hereinafter, also known as a first condition). If the first sampling value and the second sampling value do not match the first condition, the eye-width detection circuit 103 outputs a control signal CS_2. If the first sampling value and the second sampling value match the first condition, the eye-width detection circuit 103 outputs eye-width information EW of the data signal DATA.

The multiplexer 104 is coupled to the phase interpolator 101, the calibration circuit 102 and the eye-width detection circuit 103. The multiplexer 140 is configured to receive the control signal CS_1 and the control signal CS_2 and output the control signal CS_PI in response to a selection signal SEL. For example, the multiplexer 104 is controlled by the selection signal SEL to allow the control signal CS_1 or the control signal CS_2 to pass, so as to generate the control signal CS_PI.

In the present exemplary embodiment, the eye-width detector 10 is used together with a clock and data recovery circuit 11, and therefore the clock signal CLK_CDR is an output clock generated by the clock and data recovery circuit 11 in correspondence to the data signal DATA. For example, the clock and data recovery circuit 11 receives the data signal DATA and performs a phase lock operation according to the data signal DATA in order to output the clock signal CLK_CDR.

In the present exemplary embodiment, the data signal DATA is a data signal processed by an equalizer (not illustrated). For example, the data signal DATA has a plurality of pulses to transfer a series of bit data. For example, each one of the bit data refers to one bit "0" or "1". However, in an exemplary embodiment, the data signal DATA may also be a signal transferred inside any electronic devices or a data signal from one specific host system. Further, in another exemplary embodiment, it is also possible that the eye-width detector 10 is not used together with the clock and data recovery circuit 11. For example, the clock signal CLK_CDR may also be a system clock (or a reference clock) inside any electronic devices or a data clock of the data signal DATA.

In the present exemplary embodiment, the pulse waves of the data signal DATA may also be regarded as including a plurality of eyes. The eye-width information EW of the data signal DATA may be used to indicate a width of one or more of the eyes in the pulse waves of the data signal DATA (i.e., an eye-width of the data signal DATA). In general, if the eye-width of the data signal DATA is wider, it indicates that a signal quality of the data signal DATA is better (e.g., sampling for the data signal DATA will be relatively easy and accurate); otherwise, if the eye-width of the data signal DATA is narrower, it indicates that the signal quality of the data signal DATA is poorer (e.g., sampling for the data signal DATA will be relatively hard and prone to cause errors).

Figure 2:
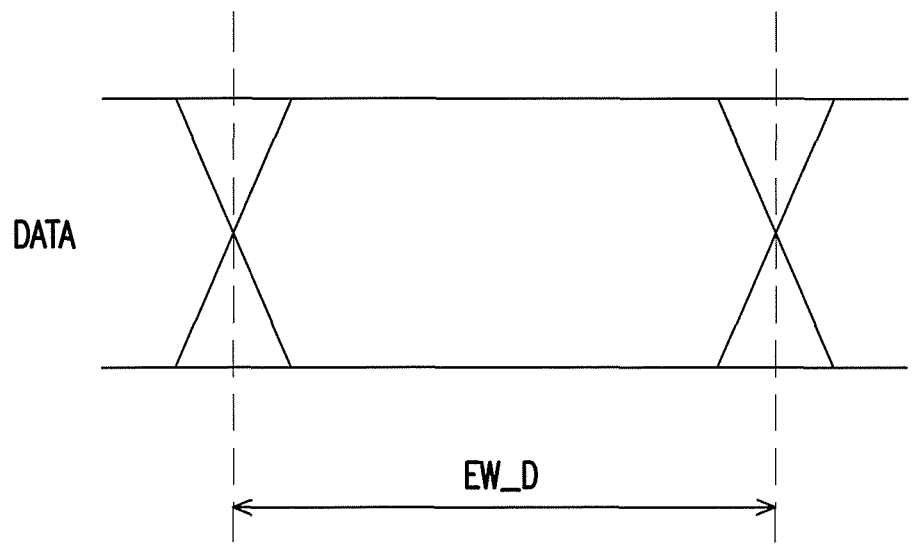
FIG. 2 is a schematic diagram illustrating the eye-width of the data signal according to an exemplary embodiment of the disclosure.

FIG. 2 is a schematic diagram illustrating the eye-width of the data signal according to an exemplary embodiment of the disclosure.

Referring to FIG. 2, as in correspondence to one eye in the currently-received data signal DATA, the eye-width information EW may be used to represent an eye-width EW_D of such eye. According to the measured eye-width EW_D, the other circuits (e.g., an equalizer, a sampling circuit, etc.) used together with the eye-width detector 10 may be informed of the signal quality of the data signal DATA. For example, according to the eye-width EW_D, the other circuits used together with the eye-width detector 10 may determine whether the current data signal DATA is suitable for sampling. If the signal is not suitable for sampling (e.g., the eye-width EW_D is less than a preset value), the eye-width EW_D of the data signal DATA may be enlarged by adjusting parameters used by an equalizer until the measured eye-width EW_D matches a filter condition. Further, the measured eye-width information EW may also be used by the other circuits to thereby perform operations such as signal quality analysis and so on.

The eye-width detector 10 of FIG. 1 is described more specifically below according to an exemplary embodiment. Referring back to FIG. 1, the multiplexer 104 is preset to receive the control signal CS_1 according to the selection signal SEL and output the corresponding control signal CS_PI. According to the clock signal CLK_CDR and the control signal CS_PI, the phase interpolator 101 performs a phase interpolation in order to generate the clock signal CLK_PI.

Specifically, in response to the received clock signal CLK_CDR, the phase interpolator 101 outputs the clock signal CLK_PI. However, the clock frequency of the clock signal CLK_PI is controlled by the control signal CS_PI. For example, the control signal CS_PI includes information of a phase stage. The phase stage is included in total phase stages usable by the phase interpolator 101. For example, if the total phase stages usable by the phase interpolator 101 are 129 stages (e.g., −64 to 64), the control signal CS_PI may instruct the phase interpolator 101 to use any one of the stages to output the clock signal CLK_PI. Each phase stage is corresponding to one delay amount. For example, the clock signal CLK_PI generated by using the phase stage at 32 stage falls behind of the clock signal CLK_PI generated by using the phase stage at 0 stage by approximately ¼ clock cycle; the clock signal CLK_PI generated by using the phase stage at 64 stage falls behind of the clock signal CLK_PI generated by using the phase stage at 0 stage by approximately ½ clock cycle; the clock signal CLK_PI generated by using the phase stage at −32 stage falls ahead of the clock signal CLK_PI generated by using the phase stage at 0 stage by approximately ¼ clock cycle; and the clock signal CLK_PI generated by using the phase stage at −64 stage falls ahead of the clock signal CLK_PI generated by using the phase stage at 0 stage by approximately ½ clock cycle. Nonetheless, the disclosure is not intended to limit an number of the total phase stages.

The calibration circuit 102 includes a calibration state machine 1021. After receiving the clock signal CLK_CDR and the clock signal CLK_PI, the calibration state machine 1021 determines whether the clock frequency of the clock signal CLK_CDR is consistent with the clock frequency of the clock signal CLK_PI. For example, the calibration state machine 1021 may determine whether one specific rising edge of the clock signal CLK_CDR is aligned with one specific rising edge of the clock signal CLK_PI; and if the two rising edges are not aligned, it indicates that the clock frequency of the clock signal CLK_CDR is inconsistent with the clock frequency of the clock signal CLK_PI, and therefore the calibration state machine 1021 outputs the control signal CS_1 which attempts to synchronize the clock frequency of the clock signal CLK_CDR and the clock frequency of the clock signal CLK_PI. For example, if the clock signal CLK_PI falls behind of the clock signal CLK_CDR, the control signal CS_1 may be used to decrease a delay amount of the clock signal CLK_PI; and if the clock signal CLK_PI falls ahead of the clock signal CLK_CDR, the control signal CS_1 may be used to increase the delay amount of the clock signal CLK_PI. According to the control signal CS_PI corresponding to the control signal CS_1, the clock frequency of the clock signal CLK_PI outputted by the phase interpolator 101 gradually becomes consistent with the clock frequency of the clock signal CLK_CDR.

Figure 3:
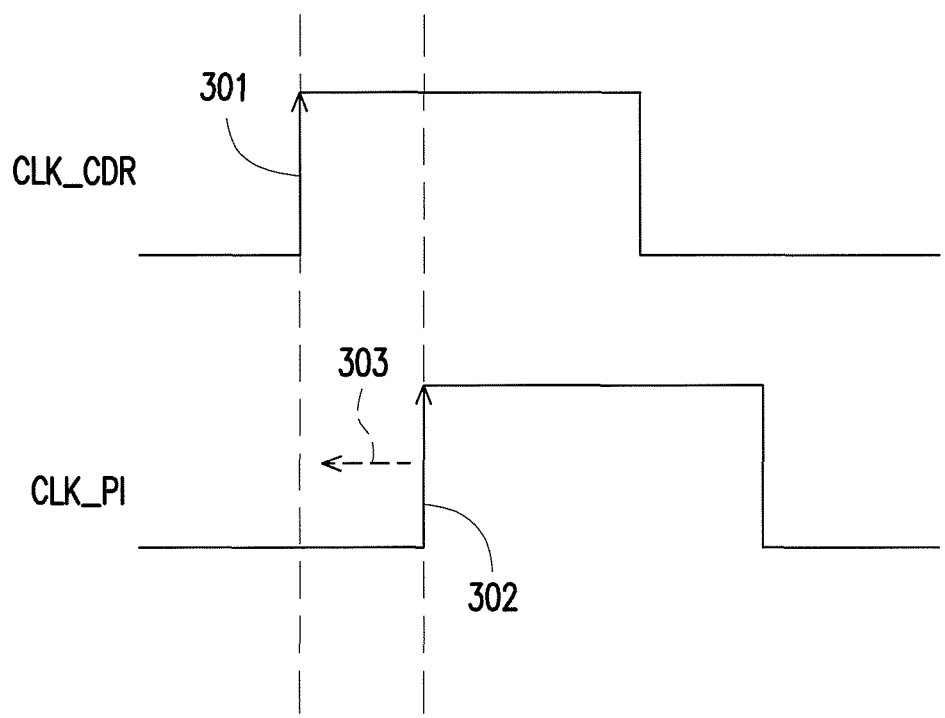
FIG. 3 illustrates a schematic diagram of adjusting the clock frequency of the clock signal according to an exemplary embodiment of the disclosure.

FIG. 3 illustrates a schematic diagram of adjusting the clock frequency of the clock signal according to an exemplary embodiment of the disclosure.

Referring to FIG. 3, it is assumed that at the beginning of receiving the clock signal CLK_CDR, the phase interpolator 101 uses the phase stage at 0 stage to generate the clock signal CLK_PI, and a rising edge 302 of the clock signal CLK_PI is not aligned with a rising edge 301 of the clock signal CLK_CDR at the time. By continuously outputting the control signal CS_1 to adjust the delay amount of the clock signal CLK_PI, the rising edge 302 of the clock signal CLK_PI is gradually aligned with the rising edge 301 of the clock signal CLK_CDR along a direction indicated by an arrow 303, such that the clock frequency of the clock signal CLK_CDR may reach (or approach) a consistency with the clock frequency of the clock signal CLK_PI.

If the clock frequency of the clock signal CLK_CDR reaches (or approaches) the consistency with the clock frequency of the clock signal CLK_PI, the calibration state machine 1021 may stop outputting the control signal CS_1. Hereinafter, the clock signal CLK_PI having the clock frequency consistent with the clock frequency of the clock signal CLK_CDR is also known as a clock signal CLK_PI_LOCK. For example, in FIG. 3, if the rising edge 302 of the clock signal CLK_PI is already aligned with the rising edge 301 of the clock signal CLK_CDR, the clock signal CLK_PI at the time may be referred to as the clock signal CLK_PI_LOCK.

Referring back to FIG. 1, if the clock signal CLK_PI is obtained, the calibration state machine 1021 further outputs a phase reference value PI_CAL (hereinafter, also known as a first phase reference value) corresponding to the clock signal CLK_PI_LOCK. The first phase reference value is corresponding to the phase stage used for generating the clock signal CLK_PI_LOCK. For example, the first phase reference value may be one phase stage used for generating the clock signal CLK_PI_LOCK itself or a reference value corresponding to that phase stage. Alternatively, in an exemplary embodiment, the first phase reference value may also be referred to as a phase calibration value.

The eye-width detection circuit 103 includes an eye-width detection state machine 1031. The eye-width detection state machine 1031 is coupled to the calibration circuit 102. The eye-width detection state machine 1031 receives the first phase reference value. According to the first phase reference value, the eye-width detection state machine 1031 is informed of how many of the phase stages has been used by the phase interpolator 101 for generating the clock signal CLK_PI_LOCK.

In the present exemplary embodiment, the first phase reference value is a trigger signal corresponding to the eye-width detection state machine 1031. For example, before receiving the first phase reference value, the eye-width detection state machine 1031 (or the eye-width detection circuit 103) is in an idle state or an inactive state. If the first phase reference value is received, the eye-width detection state machine 1031 (or the eye-width detection circuit 103) is activated to instantly output a control signal CS_3 corresponding to the first phase reference value. Meanwhile, the multiplexer 104 receives the control signal CS_3 and outputs the corresponding control signal CS_PI in response to the selection signal SEL. However, in another exemplary embodiment, when the first phase reference value is not yet received, the eye-width detection state machine 1031 (or the eye-width detection circuit 103) may also be in any working state waiting for the first phase reference value.

In the present exemplary embodiment, the control signal CS_3 is configured to delay or accelerate the clock signal CLK_PI_LOCK by ¼ clock cycle. For example, it is assumed that the phase interpolator 101 originally uses one specific phase stage to output the clock signal CLK_PI_LOCK; after receiving the control signal CS_PI corresponding to the control signal CS_3, the phase interpolator 101 is changed to delay or accelerate the clock signal CLK_PI_LOCK by ¼ clock cycle by using another phase stage. For example, assuming that the total phase stages usable by the phase interpolator 101 is N stages, a number of the phase stages instructed by the control signal CS_3 may be N/4 or (N/4)−1 stage more (or less) than a number of the phase stage originally used for generating the clock signal CLK_PI_LOCK.

Figure 4:
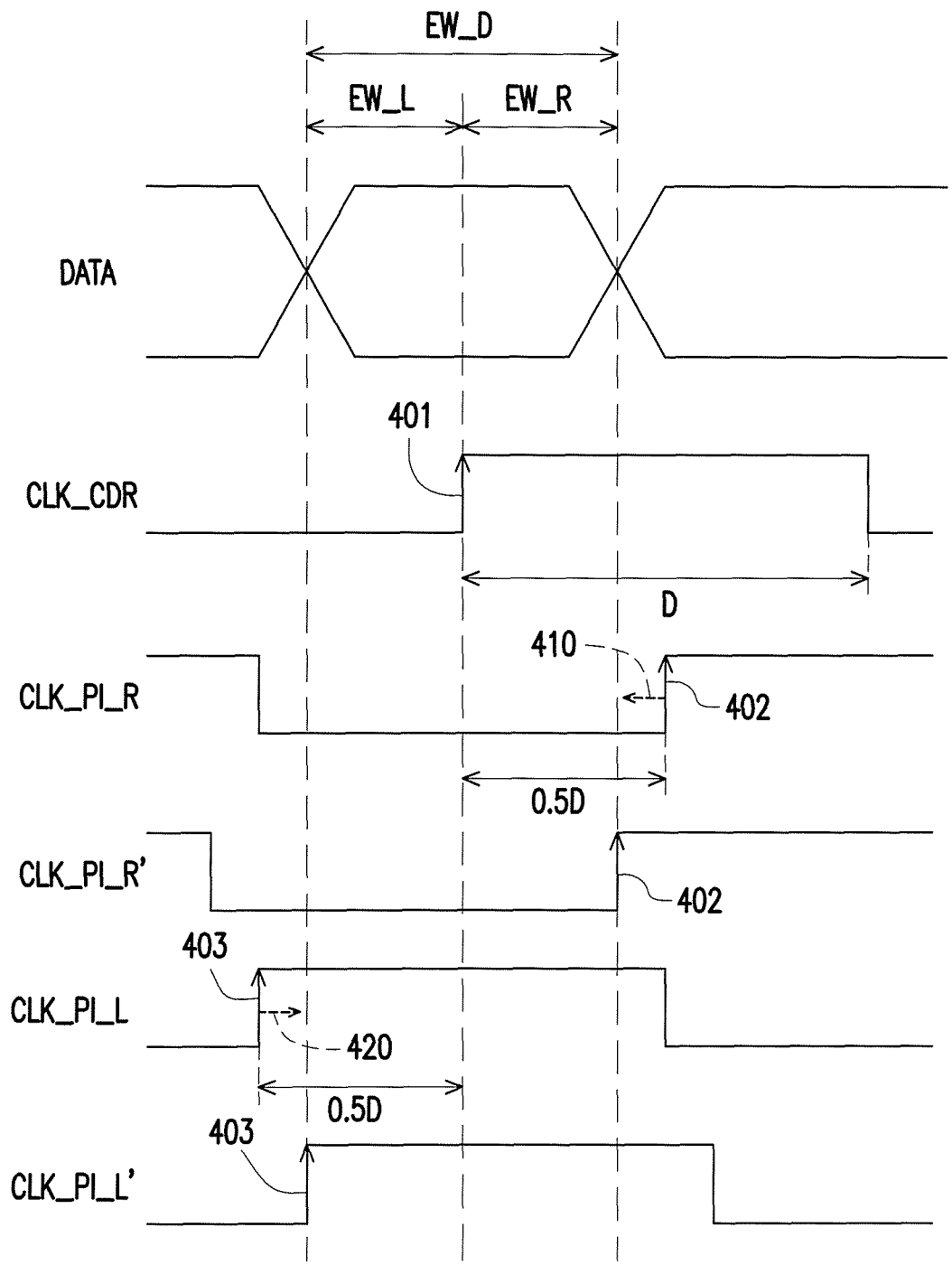
FIG. 4 is a schematic diagram illustrating the data signal and the clock signal according to an exemplary embodiment of the disclosure.

FIG. 4 is a schematic diagram illustrating the data signal and the clock signal according to an exemplary embodiment of the disclosure.

Referring to FIG. 4, it is assumed that a rising edge 401 of the clock signal CLK_CDR is already locked at a center of one eye of the data signal DATA (e.g., suitable for sampling the data signal DATA) and the clock signal CLK_PI is already aligned with the clock signal CLK_CDR (i.e., the clock signal CLK_PI_LOCK is obtained). In this case, the eye-width detection state machine 1031 records the first phase reference value corresponding to the clock signal CLK_PI_LOCK and accordingly outputs the control signal CS_3. If the control signal CS_3 instructs to accelerate the clock signal CLK_PI_LOCK by ¼ clock cycle, the clock signal CLK_PI generated by the phase interpolator 101 in correspondence to the clock signal CS_3 is represented by a clock signal CLK_PI_R in FIG. 4; and if the control signal CS_3 instructs to delay the clock signal CLK_PI_LOCK by ¼ clock cycle, the clock signal CLK_PI generated by the phase interpolator 101 in correspondence to the clock signal CS_3 is represented by a clock signal CLK_PI_L in FIG. 4.

In FIG. 4, assuming that one width of one pulse wave of the clock signal CLK_CDR (or the clock signal CLK_PI_LOCK) is D, an initial difference between a rising edge 402 of the clock signal CLK_PI_R and the rising edge 401 of the clock signal CLK_PI is approximately 0.5 D, and an initial difference between a rising edge 403 of the clock signal CLK_PI_L and the rising edge 401 of the clock signal CLK_PI is also approximately 0.5 D.

In the present exemplary embodiment, the clock signal CLK_PI_R is used to measure a right-half eye-width EW_R, and the clock signal CLK_PI_L is used to measure a left-half eye-width EW_L. In the present exemplary embodiment, it is assumed that the right-half eye-width EW_R is to be measured first, and therefore the control signal CS_3 is configured to generate the clock signal CLK_PI_R. However, in another exemplary embodiment, if the left-half eye-width EW_L is to be measured first, the control signal CS_3 is configured to generate the clock signal CLK_PI_L.

In correspondence to the control signal CS_3 being outputted, the eye-width detection state machine 1031 generates (or starts to generate) the corresponding sampling signal pair and determines whether the first sampling value and the second sampling value in the generated sampling signal pair match the first condition. Herein, the first sampling value is obtained by sampling the data signal DATA by using the clock signal CLK_CDR, and the second sampling value is obtained by sampling the data signal DATA by using the clock signal CLK_PI_R. If the first sampling value and the second sampling value do not match the first condition, the eye-width detection state machine 1031 outputs the control signal CS_2.

For example, in the present exemplary embodiment, if the first sampling value is obtained by sampling the data signal DATA by using the rising edge 401 of the clock signal CLK_CDR and the second sampling value is obtained by sampling the data signal DATA by using the rising edge 402 of the clock signal CLK_PI_R, the control signal CS_2 is configured to instruct for decreasing a delay amount of the clock signal CLK_PI_R. Alternatively, in another exemplary embodiment, if the first sampling value is obtained by sampling the data signal DATA by using the rising edge 401 of the clock signal CLK_CDR and the second sampling value is obtained by sampling the data signal DATA using the rising edge 403 of the clock signal CLK_PI_L, the control signal CS_2 is configured to instruct for increasing the delay amount of the clock signal CLK_PI_R. The disclosure is not intended to limit whether the control signal CS_2 being sent each time is configured to increase or decrease how much of the delay amount.

In an exemplary embodiment, if a sampling time corresponding to the first sampling value is referred to as a first time-point and a sampling time corresponding to the second sampling value is referred to as a second time-point, the control signal CS_2 is configured to reduce a time difference between the first time-point and the second time-point. Take FIG. 4 as an example, the first time-point may be a time-point for sampling the data signal DATA by using the rising edge 401 of the clock signal CLK_CDR; the second time-point may be a time-point for sampling the data signal DATA by using the rising edge 402 of the clock signal CLK_PI_R or the rising edge 403 of the clock signal CLK_PI_L; and the control signal CS_2 is configured to make the first time-point and the second time-point closer to each other.

The eye-width detection state machine 1031 continuously determines whether the first sampling value and the second sampling value, which are repeatedly obtained, match the first condition and outputs the control signal CS_2 if determining that the first sampling value and the second sampling value do not match the first condition. In response to the selection signal SEL, the multiplexer 104 also receives the control signal CS_2 and outputs the corresponding control signal CS_PI. For example, in the present exemplary embodiment, according to the received control signal CS_PI, the rising edge 402 of the clock signal CLK_PI_R outputted by the phase interpolator 101 moves along a direction indicated by an arrow 410 (i.e., to the left). Alternatively, in another exemplary embodiment, according to the received control signal CS_PI, the rising edge 403 of the clock signal CLK_PI_L outputted by the phase interpolator 101 moves along a direction indicated by an arrow 420 (i.e., to the right).

If the eye-width detection state machine 1031 determines that the obtained first sampling value and the obtained second sampling value match the first condition, the eye-width detection state machine 1031 may stop outputting the control signal CS_2. Meanwhile, the eye-width detection state machine 1031 obtains another phase reference value (hereinafter, also known as a second phase reference value) corresponding to the current clock signal CLK_PI_R.

For example, in the present exemplary embodiment, after moving the clock signal CLK_PI_R to a position of a clock signal CLK_PI_R', the first sampling value obtained by sampling the data signal CLK_CDR and the second sampling value obtained by sampling the data signal DATA by using the rising edge 402 of the clock signal CLK_PI_R' match the first condition. At this time, the eye-width detection state machine 1031 obtains and records the second phase reference value corresponding to the clock signal CLK_PI_R'. The second phase reference value is corresponding to a phase stage used for generating the clock signal CLK_PI_R'. For example, the second phase reference value may be one phase stage used for generating the clock signal CLK_PI_R' itself or a reference value corresponding to that phase stage. Alternatively, in another exemplary embodiment of FIG. 4, after moving the clock signal CLK_PI_L to a position of the clock signal CLK_PI_L', the first sampling value obtained by sampling the data signal DATA by using the rising edge 401 of the clock signal CLK_CDR and the second sampling value obtained by sampling the data signal DATA by using the rising edge 403 of the clock signal CLK_PI_L' also match the first condition. At this time, the second phase reference value recorded by the eye-width detection state machine 1031 is corresponding to the clock signal CLK_PI_U.

In the present exemplary embodiment, according to the first phase reference value and the second phase reference value, the eye-width detection state machine 1031 directly set a difference between the first phase reference value and the second phase reference value to be the right-half eye-width EW_R. Alternatively, the eye-width detection state machine 1031 may also multiply the difference between the first phase reference value and the second phase reference value by a weight in order to obtain the right-half eye-width EW_R. For example, the weight may be obtained by dividing a first parameter by a second parameter. For example, the first parameter is the width D of aforesaid pulse wave, and the second parameter is the number of the total phase stages usable by the phase interpolator 101. After obtaining the right-half eye-width EW_R, the eye-width detection state machine 1031 may directly multiply the right-half eye-width EW_R by 2 to obtain the eye-width EW_D.

Alternatively, according to another exemplary embodiment of FIG. 4, after obtaining the right-half eye-width EW_R, it is also possible that the left-half eye-width EW_L may be found by generating the clock signal CLK_PI_L and gradually moving the rising edge 403 of the clock signal CLK_PI_L along the direction indicated by the arrow 420 to fall within a range of the left-half eye-width EW_L, so as to obtain the eye-width EW_D (i.e., EW_D=EW_R+EW_L). The operation of generating and adjusting the clock signal CLK_PI_L into the clock signal CLK_PI_L' to find the left-half eye-width EW_L is similar to aforesaid operation of generating and adjusting the clock signal CLK_PI_R into the clock signal CLK_PI_R' to find the right-half eye-width EW_R, which is not repeated hereinafter.

Further, in another exemplary embodiment, the left-half eye-width EW_L may be found first and then the left-half eye-width EW_L is multiplied by 2 to obtain the eye-width EW_D. Alternatively, in another exemplary embodiment, the left-half eye-width EW_L may be found first and then finding the right-half eye-width EW_R, so as to obtain the eye-width EW_D. After obtaining the eye-width EW_D, the eye-width detection state machine 1031 outputs the eye-width information EW of the data signal DATA.

In an exemplary embodiment, the eye-width detection state machine 1031 further performs an eye-height detection to obtain an eye-height of the data signal DATA. Take FIG. 2 as an example, a transverse (or horizontal) width of one eye in the data signal DATA is known as the eye-width (e.g., EW_D), and the eye-height of one eye in the data signal DATA is referred to as a longitudinal (or vertical) width of the eye. For example, the eye-width detection state machine 1031 may include an eye-height detection circuit (not illustrated) capable of synchronously detecting the eye-height of the data signal DATA and outputting eye-height information of the data signal DATA. However, in another exemplary embodiment, the eye-width detector 10 or the electronic device to which the eye-width detector 10 belongs does not detect the eye-height of the data signal DATA, such that a speed for outputting the data signal DATA (or the eye-width information EW) may be accelerated and a processing efficiency for the data signal DATA may be improved.

Figure 5:
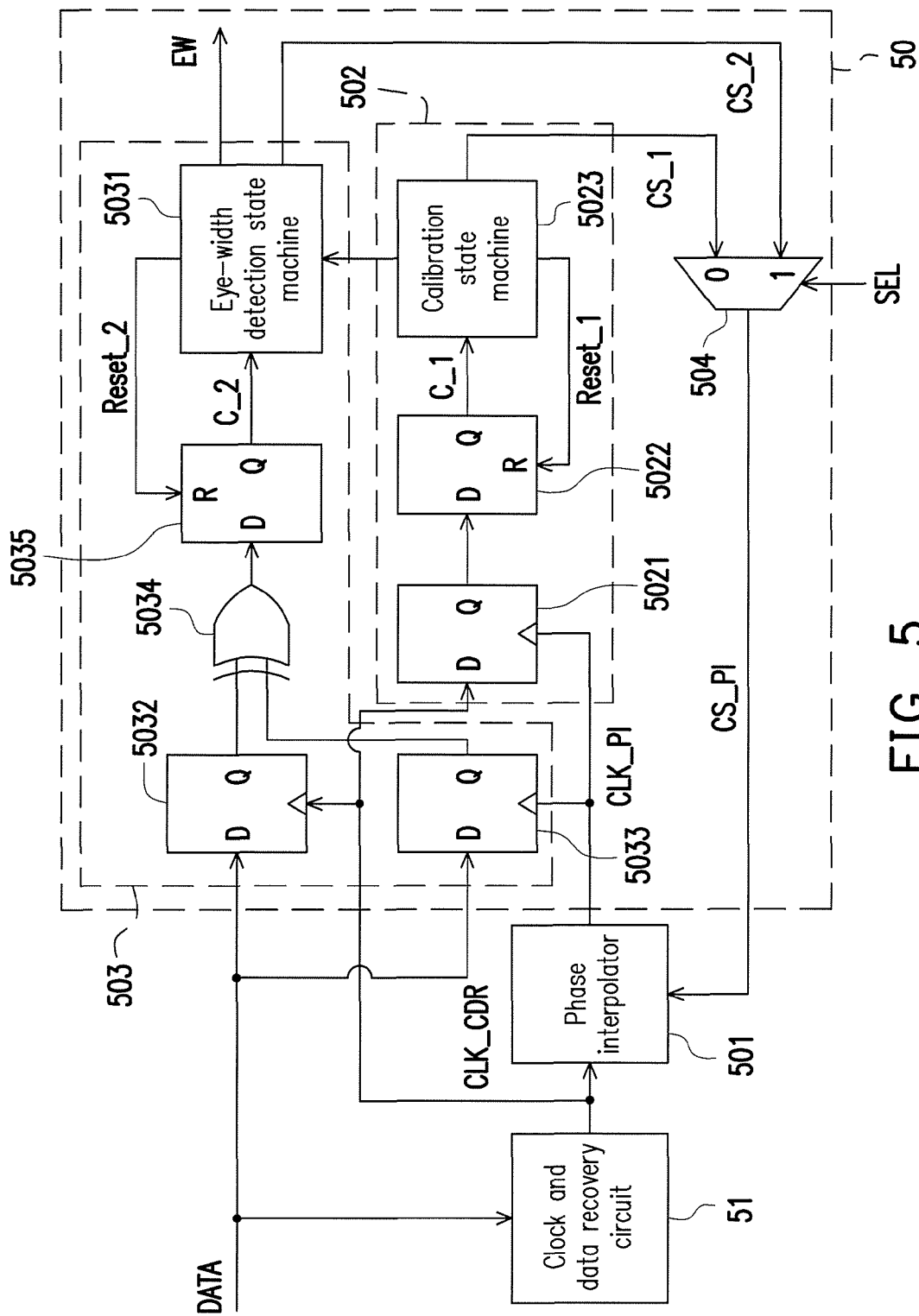
FIG. 5 is a schematic diagram illustrating the eye-width detector according to another exemplary embodiment of the disclosure.

FIG. 5 is a schematic diagram illustrating the eye-width detector according to another exemplary embodiment of the disclosure.

Referring to FIG. 5, an eye-width detector 50 is used together with a clock and data recovery circuit 51. The clock and data recovery circuit 51 is identical or similar to the clock and data recovery circuit 11 of FIG. 1. The clock and data recovery circuit 51 receives the data signal DATA and outputs the clock signal CLK_CDR.

The eye-width detector 50 includes a phase interpolator 501, a calibration circuit 502, an eye-width detection circuit 503 and a multiplexer 504. Herein, the phase interpolator 501 and the multiplexer 504 are identical or similar to the phase interpolator 101 and the multiplexer 104 of FIG. 1, respectively.

The calibration circuit 502 includes a flip-flop circuit 5021, a latch circuit 5022 and a calibration state machine 5023.

The flip-flop circuit 5021 is coupled to the phase interpolator 501. The flip-flop circuit 5021 is configured to perform a sampling operation according to the clock signal CLK_CDR and the clock signal CLK_PI. For example, if one of the clock signal CLK_CDR and the clock signal CLK_PI is logic high and another one of the clock signal CLK_CDR and the clock signal CLK_PI is logic low, the flip-flop circuit 5021 outputs a first value (e.g., 0). If both the clock signal CLK_CDR and the clock signal CLK_PI are logic high or both the clock signal CLK_CDR and the clock signal CLK_PI are logic low, the flip-flop circuit 5021 outputs a second value (e.g., 1). The first value is different from the second value.

The latch circuit 5022 is coupled between the flip-flop circuit 5021 and the calibration state machine 5023. The latch circuit 5022 is configured to receive an output of the flip-flop circuit 5021 and accordingly output a first comparison signal C_1.

The calibration state machine 5023 determines whether the clock frequency of the clock signal CLK_CDR is consistent with the clock frequency of the clock signal CLK_PI according to the comparison signal C_1. For example, if the comparison signal C_1 is the first value (e.g., 0), the calibration state machine 5023 determines that the clock frequency of the clock signal CLK_CDR is inconsistent with the clock frequency of the clock signal CLK_PI. If determining that the clock frequency of the clock signal CLK_CDR is inconsistent with the clock frequency of the clock signal CLK_PI, the calibration state machine 5023 outputs the control signal CS_1 to the multiplexer 504 and issues a reset signal Reset_1 to reset the latch circuit 5022. However, if the comparison signal C_1 is the second value (e.g., 1), the calibration state machine 5023 determines that the clock frequency of the clock signal CLK_CDR is consistent with the clock frequency of the clock signal CLK_PI. If determining that the clock frequency of the clock signal CLK_CDR is consistent with the clock frequency of the clock signal CLK_PI, the calibration state machine 5023 outputs the first phase reference value corresponding to the current clock signal CLK_PI to the eye-width detection circuit 503. Meanwhile, the calibration state machine 5023 may stop outputting (or changing) the control signal CS_1. In addition, the calibration state machine 5023 is identical or similar to the calibration state machine 1021 of FIG. 1, and thus the identical or similar parts are not repeated hereinafter.

The eye-width detection circuit 503 includes an eye-width detection state machine 5031, a sampling circuit 5032, a sampling circuit 5033, an Exclusive-OR (XOR) circuit 5034 and a latch circuit 5035.

The eye-width detection state machine 5031 is configured to receive the first phase reference value and activated in response to the first phase reference value. For example, the eye-width detection state machine 5031 outputs the control signal CS_3 corresponding to the first phase reference value according to the first phase reference value.

The sampling circuit 5032 is coupled to the clock and data recovery circuit 51. The sampling circuit 5032 is configured to receive the data signal DATA and the clock signal CLK_CDR and use the clock signal CLK_CDR to sample the data signal DATA in order to output a sampling value S_1 (i.e., aforesaid first sampling value).

The sampling circuit 5033 is coupled to the phase interpolator 501. The sampling circuit 5033 is configured to receive the data signal DATA and the clock signal CLK_PI and use the clock signal CLK_PI to sample the data signal DATA in order to output a sampling value S_2 (i.e., aforesaid second sampling value).

In the present exemplary embodiment, each of the sampling circuit 5032 and the sampling circuit 5033 may also be implemented by at least one sense amplify circuit, and each of the sampling circuit 5032 and the sampling circuit 5033 may also perform a sense amplification on the data signal DATA by using the received clock signal CLK_CDR and the received clock signal CLK_PI, respectively.

The XOR circuit 5034 is coupled to the sampling circuit 5032 and the sampling circuit 5033. The XOR circuit 5034 is configured to perform an XOR operation according to the sampling value S_1 and the sampling value S_2. For example, if the sampling value S_1 and the sampling value S_2 are not equal, the XOR circuit 5034 outputs a third value (e.g., 1); and if the sampling value S_1 and the sampling value S_2 are equal, the XOR circuit 5034 outputs a fourth value (e.g., 0).

The latch circuit 5035 is coupled between the XOR circuit 5034 and the eye-width detection state machine 5031. The latch circuit 5035 is configured to receive an output of the XOR circuit 5034 and output a corresponding comparison signal C_2.

The eye-width detection state machine 5031 receives the comparison signal C_2 and determines whether the sampling value S_1 and the sampling value S_2 are equal according to the comparison signal C_2. For example, if the comparison signal C_2 is the third value (e.g., 1), the eye-width detection state machine 5031 determines that the sampling value S_1 and the sampling value S_2 are not equal; and if the comparison signal C_2 is the fourth value (e.g., 0), the eye-width detection state machine 5031 determines that the sampling value S_1 and the sampling value S_2 are equal.

If the eye-width detection state machine 5031 determines that the sampling value S_1 and the sampling value S_2 are not equal, the eye-width detection state machine 5031 outputs the control signal CS_2 and issues a reset signal Reset_2 to reset the latch circuit 5035. If the eye-width detection state machine 5031 determines that the sampling value S_1 and the sampling value S_2 are equal, the eye-width detection state machine 5031 outputs the eye-width information EW of the data signal DATA according to the first phase reference value and the second phase reference value corresponding to the current clock signal CLK_PI. Nevertheless, the eye-width detection state machine 5031 is identical or similar to the eye-width detection state machine 1031 of FIG. 1, and thus the identical or similar parts are not repeated hereinafter.

It is worth mentioning that, each of FIG. 1 and FIG. 5 simply illustrates a schematic circuit configuration and a component coupling relation for the eye-width detector, rather than limits that the schematic circuit configuration and the component coupling relation for the eye-width detector must be configured according to any one of FIG. 1 and FIG. 5. For example, in any exemplary embodiment of FIG. 1 and FIG. 5, more circuit components may be added into the corresponding eye-width detector to accomplish more preferable technical effects or provide additional functions. Alternatively, in any exemplary embodiment of FIG. 1 and FIG. 5, the coupling relation between the circuit components may also be changed.

Figure 6:
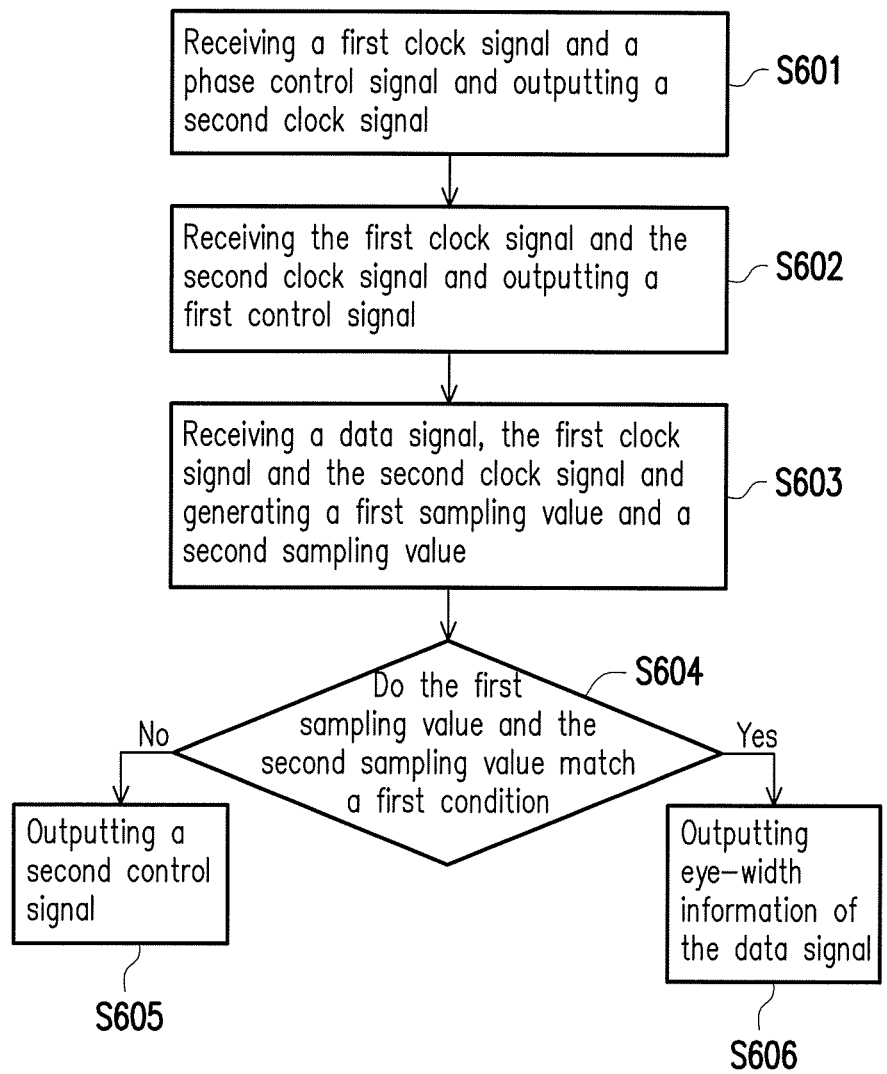
FIG. 6 is a flowchart illustrating an eye-width detection method according to an exemplary embodiment of the disclosure.

FIG. 6 is a flowchart illustrating an eye-width detection method according to an exemplary embodiment of the disclosure. Details regarding the flowchart of FIG. 6 are provided below with reference to the eye-width detector 10 of FIG. 1. However, the flowchart of FIG. 6 may also be used by using the other eye-width detectors.

Referring to FIG. 1 and FIG. 6 together, in step S601, the phase interpolator 101 receives the clock signal CLK_CDR (also known as a first clock signal) and the control signal CS_PI (also known as a phase control signal) and outputs the clock signal CLK_PI (also known as a second clock signal). In step S602, the calibration circuit 102 receives the clock signal CLK_CDR and the clock signal CLK_PI and outputs the control signal CS_1 (also known as a first control signal). In step S603, the eye-width detection circuit 103 receives the data signal DATA, the clock signal CLK_CDR and the clock signal CLK_PI and generates the first sampling value and the second sampling value. In step S604, the eye-width detection circuit 103 determines whether the first sampling value and the second sampling value match the first condition. If the first sampling value and the second sampling value do not match the first condition, the eye-width detection circuit 103 outputs the control signal CS_2 (also known as a second control signal) in step S605. If the first sampling value and the second sampling value match the first condition, the eye-width detection circuit 103 outputs the eye-width information EW of the data signal DATA in step S606. Herein, the control signal CS_PI may be outputted by the multiplexer 104 in correspondence to the control signal CS_1 or the control signal CS_2.

Figure 7:
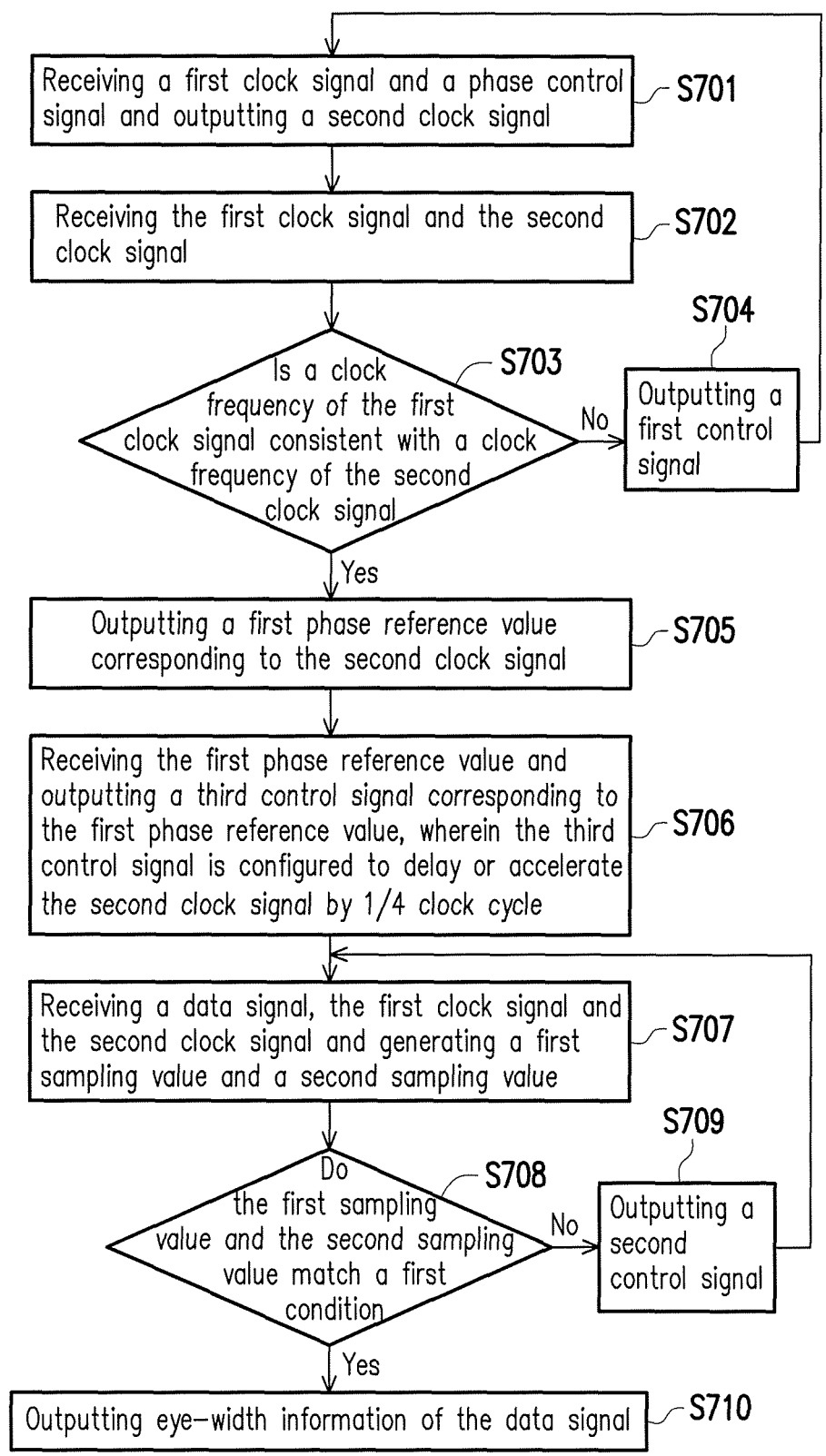
FIG. 7 is a flowchart illustrating an eye-width detection method according to another exemplary embodiment of the disclosure.

FIG. 7 is a flowchart illustrating an eye-width detection method according to another exemplary embodiment of the disclosure. Details regarding the flowchart of FIG. 7 are also provided below with reference to the eye-width detector 10 of FIG. 1. However, the flowchart of FIG. 7 may also be used by using the other eye-width detectors.

Referring to FIG. 7, in step S701, the phase interpolator 101 receives the clock signal CLK_CDR and the control signal CS_PI and outputs the clock signal CLK_PI. In step S702, the calibration circuit 102 receives the clock signal CLK_CDR and the clock signal CLK_PI. In step S703, the calibration circuit 102 determines whether the clock frequency of the clock signal CLK_CDR is consistent with the clock frequency of the clock signal CLK_PI. If the clock frequency of the clock signal CLK_CDR is inconsistent with the clock frequency of the clock signal CLK_PI, the calibration circuit 102 outputs the control signal CS_1 in step S704. If the clock frequency of the clock signal CLK_CDR is consistent with the clock frequency of the clock signal CLK_PI, the calibration circuit 102 outputs the phase reference value PI_CAL (also known as a first phase reference value) corresponding to the clock signal CLK_PI in step S705. In step S706, the eye-width detection circuit 103 receives the first phase reference value and outputs the control signal C_3 (also known as a third control signal) corresponding to the first phase reference value, wherein the control signal CS_3 is configured to delay or accelerate the clock signal CLK_PI by ¼ clock cycle. In step S707, the eye-width detection circuit 103 receives the data signal DATA, the clock signal CLK_CDR and the clock signal CLK_PI and generates the first sampling value and the second sampling value. In step S708, the eye-width detection circuit 103 determines whether the first sampling value and the second sampling value match the first condition. If the first sampling value and the second sampling value do not match the first condition, the eye-width detection circuit 103 outputs the control signal CS_2 in step S709. If the first sampling value and the second sampling value match the first condition, the eye-width detection circuit 103 outputs the eye-width information EW of the data signal DATA in step S710.

Nevertheless, each of steps depicted in FIG. 6 and FIG. 7 have been described in detail as above, thus related description thereof is not repeated hereinafter. It should be noted that, the steps depicted in FIG. 6 and FIG. 7 may be implemented as a plurality of program codes or circuits, which are not particularly limited in the disclosure. Moreover, the methods disclosed in FIG. 6 and FIG. 7 may be implemented with reference to above embodiments, or may be implemented separately, which are not particularly limited in the disclosure.

In an exemplary embodiment, the eye-width detectors 10 or 50 are suitable to be disposed in a memory storage device. Generally, the memory storage device (also known as a memory storage system) includes a rewritable non-volatile memory module and a controller (also known as a control circuit). The memory storage device is usually configured together with a host system so that the host system may write data into the memory storage device or read data from the memory storage device.

Figure 8:
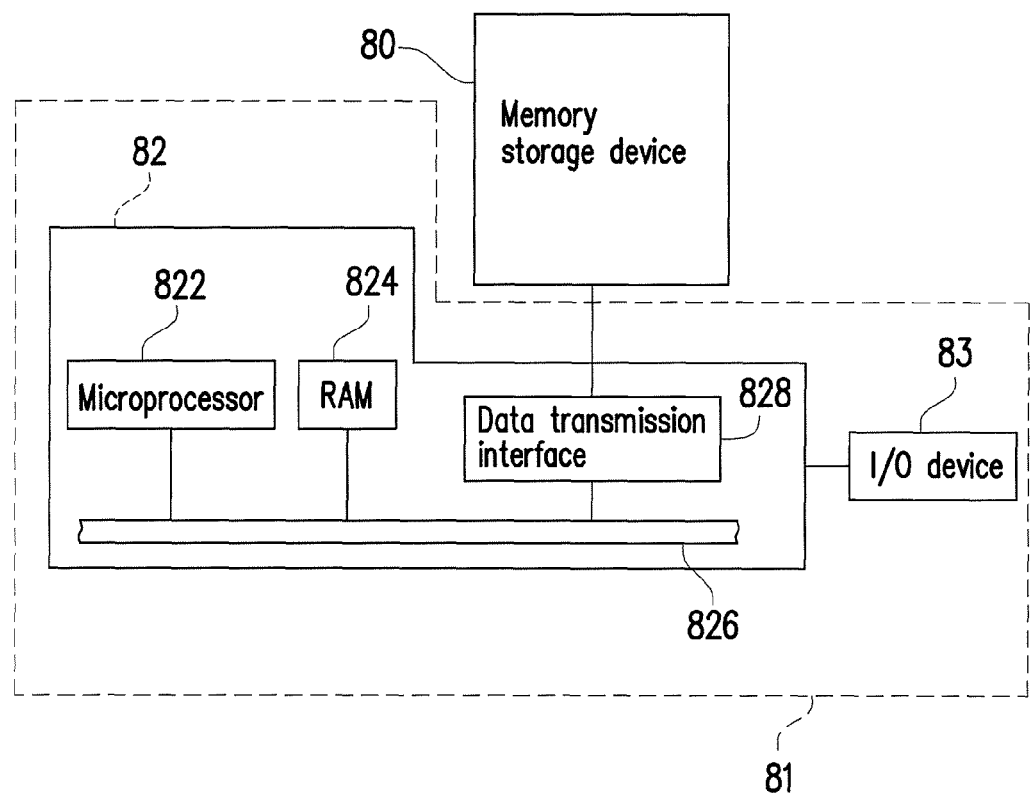
FIG. 8 is a schematic diagram illustrating a host system and a memory storage device according to an exemplary embodiment of the disclosure.
Figure 9:
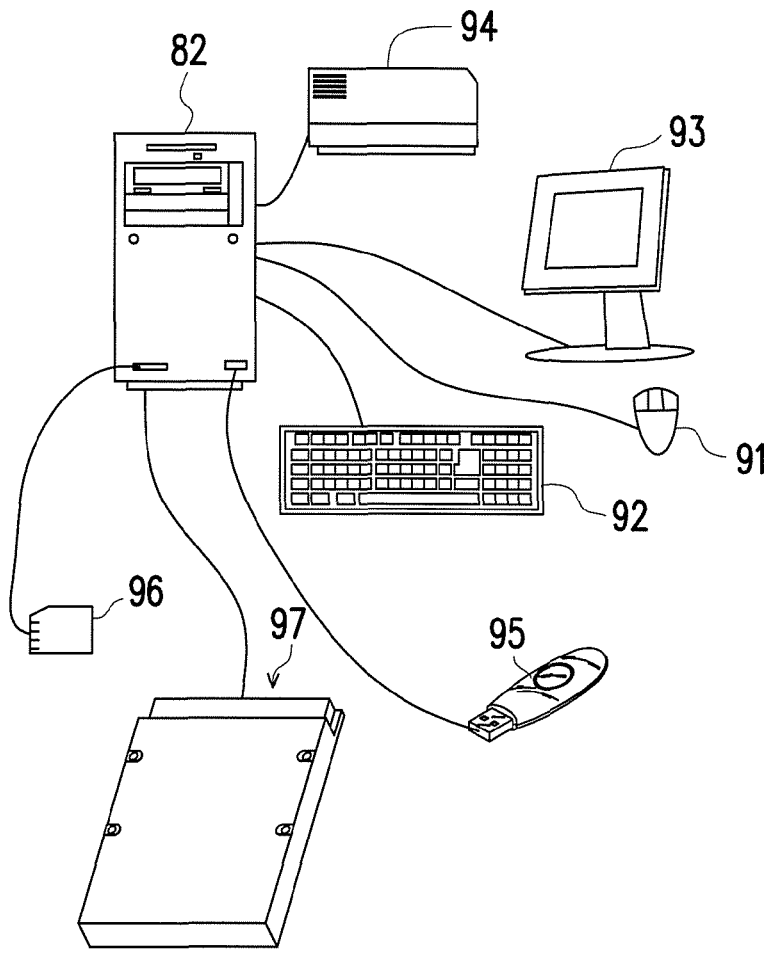
FIG. 9 is a schematic diagram of a computer, an input/output device, and a memory storage device according to an exemplary embodiment of the disclosure.
Figure 10:
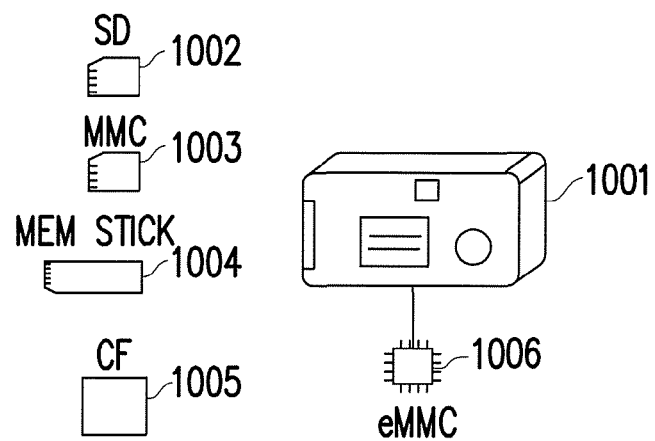
FIG. 10 is a schematic diagram illustrating a host system and a memory storage device according to an exemplary embodiment of the disclosure.

FIG. 8 is a schematic diagram illustrating a host system and a memory storage device according to an exemplary embodiment of the disclosure. FIG. 9 is a schematic diagram of a computer, an input/output device, and a memory storage device according to an exemplary embodiment of the disclosure. FIG. 10 is a schematic diagram illustrating a host system and a memory storage device according to an exemplary embodiment of the disclosure.

Referring to FIG. 8, a host system 81 generally includes a computer 82 and an input/output (I/O) device 83. The computer 82 includes a microprocessor 822, a random access memory (RAM) 824, a system bus 826, and a data transmission interface 828. For example, the I/O device 83 includes a mouse 91, a keyboard 92, a display 93 and a printer 94 as shown in FIG. 9. It should be understood that the devices illustrated in FIG. 9 are not intended to limit the I/O device 83, and the I/O device 83 may further include other devices.

In an exemplary embodiment, the memory storage device 80 is coupled to other devices of the host system 81 through the data transmission interface 828. By using the microprocessor 822, the random access memory 824 and the Input/Output (I/O) device 83, data may be written into the memory storage device 80 or may be read from the memory storage device 80. For example, the memory storage device 80 may be a rewritable non-volatile memory storage device such as a flash drive 95, a memory card 96, or a solid state drive (SSD) 97 as shown in FIG. 9.

Generally, the host system 81 may substantially be any system capable of cooperating with the memory storage device 80 for storing data. Even though the host system 81 is illustrated as a computer system in the present exemplary embodiment, however, in another exemplary embodiment of the present disclosure, the host system 81 may be a digital camera, a video camera, a telecommunication device, an audio player, or a video player. For example, when the host system is a digital camera (video camera) 1001, the rewritable non-volatile memory storage device may be a SD card 1002, a MMC card 1003, a memory stick 1004, a CF card 1005 or an embedded storage device 1006 (as shown by FIG. 10). The embedded storage device 1006 includes an embedded MMC (eMMC). It should be mentioned that the eMMC is directly coupled to a substrate of the host system.

Figure 11:
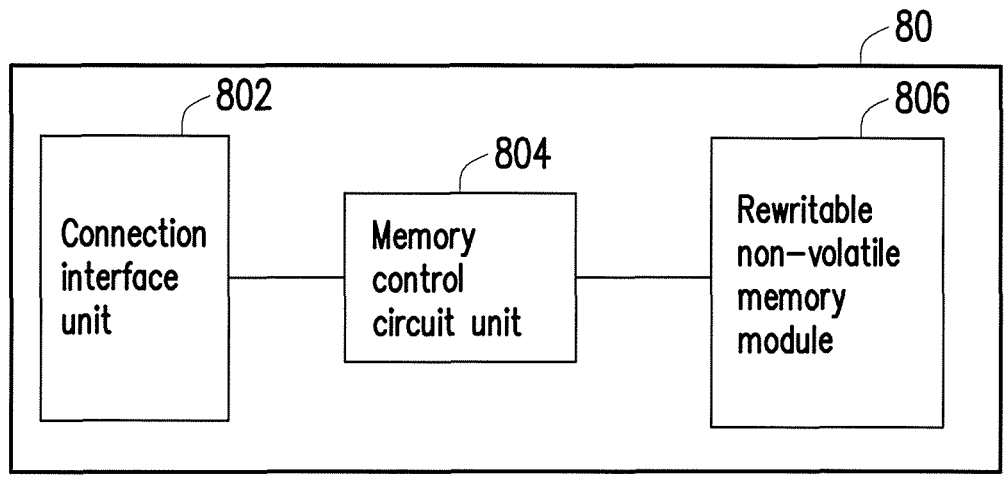
FIG. 11 is a schematic block diagram illustrating the memory storage device depicted in FIG. 8.

FIG. 11 is a schematic block diagram illustrating the memory storage device depicted in FIG. 8.

Referring to FIG. 11, the memory storage device 80 includes a connection interface unit 802, a memory control circuit unit 804 and a rewritable non-volatile memory module 806.

In the present exemplary embodiment, the connection interface unit 802 is compatible with a serial advanced technology attachment (SATA) standard. However, the disclosure is not limited thereto, and the connection interface unit 802 may also be compatible to a Parallel Advanced Technology Attachment (PATA) standard, an Institute of Electrical and Electronic Engineers (IEEE) 1394 standard, a peripheral component interconnect (PCI) Express interface standard, a universal serial bus (USB) standard, a secure digital (SD) interface standard, a Ultra High Speed-I (UHS-I) interface standard, a Ultra High Speed-II (UHS-II) interface standard, a memory sick (MS) interface standard, a multi media card (MMC) interface standard, an embedded MMC (eMMC) interface standard, a Universal Flash Storage (UFS) interface standard, a compact flash (CF) interface standard, an integrated device electronics (IDE) interface standard or other suitable standards. The connection interface unit 802 and the memory control circuit unit 804 may be packaged into one chip, or the connection interface unit 802 is distributed outside of a chip containing the memory control circuit unit 804.

The memory control circuit unit 804 is configured to execute a plurality of logic gates or control commands which are implemented in a hardware form or in a firmware form and execute operations of writing, reading or erasing data in the rewritable non-volatile memory storage module 806 according to the commands of the host system 81.

The rewritable non-volatile memory module 806 is coupled to the memory control circuit unit 804 and configured to store data written from the host system 81. The rewritable non-volatile memory module 806 may be a Single Level Cell (SLC) NAND flash memory module (i.e., a flash memory module capable of storing one bit data in one memory cell), a Multi Level Cell (MLC) NAND flash memory module (i.e., a flash memory module capable of storing two bit data in one memory cell), a Triple Level Cell (TLC) NAND flash memory module (i.e., a flash memory module capable of storing three bit data in one memory cell), other flash memory modules or any memory module having the same features.

In an exemplary embodiment, the eye-width detectors 10 or 50 are disposed in the connection interface unit 802, so as to detect the eye-width of the data signal DATA transmitted in the connection interface unit 802 and accordingly output the eye-width information EW of the data signal DATA. For example, the eye-width information EW of the data signal DATA may be used by other electronic components (e.g., the equalizer and/or the sampling circuit) in the connection interface unit 802 or the memory control circuit unit 804. If the detection of the eye-width information of the data signal DATA may be more accurate and/or completed with faster speed, analyzing and/or sampling capability of the connection interface unit 802 for the signals from the host system 81 may also be improved. Further, in an exemplary embodiment, the clock and data recovery circuits 11 or 51 may also be disposed in the connection interface unit 802.

Figure 12:
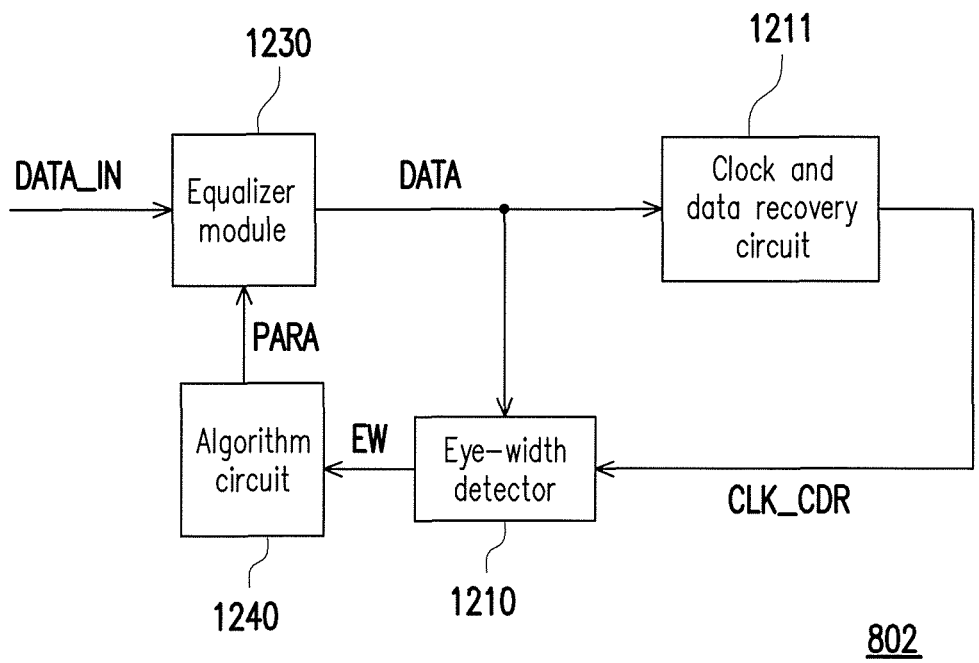
FIG. 12 is a schematic block diagram illustrating a connection interface unit according to an exemplary embodiment of the disclosure.

FIG. 12 is a schematic block diagram illustrating a connection interface unit according to an exemplary embodiment of the disclosure.

Referring to FIG. 12, the connection interface unit 802 includes an eye-width detector 1210, a clock and data recovery circuit 1211, an equalizer module 1230 and an algorithm circuit 1240.

The eye-width detector 1210 is configured to receive the data signal DATA and the clock signal CLK_CDR and output the eye-width information EW of the data signal DATA. The clock and data recovery circuit 1211 is coupled to the eye-width detector 1210. The clock and data recovery circuit 1211 is configured to receive the data signal DATA and output the clock signal CLK_CDR. The eye-width detector 1210 and the clock and data recovery circuit 1211 are identical or similar to the eye-width detectors and the clock and data recovery circuits as mentioned in the foregoing exemplary embodiments respectively, and thus identical or similar parts are not repeated hereinafter. In addition, the clock signal CLK_CDR may also be used by other electronic components in the connection interface unit 802. For example, a sampling circuit (not illustrated) in the connection interface unit 802 may sample the data signal DATA according to the clock signal CLK_CDR and the connection interface unit 802 may transmit a sampling data sequence obtained from the sampling to the memory control circuit unit 804.

The equalizer module 1230 is coupled to the eye-width detector 1210 and the algorithm circuit 1211. The equalizer module 1230 is configured to receive an input signal DATA_IN. In the present exemplary embodiment, the input signal DATA_IN is a data signal from the host system 81. The input signal DATA_IN may be a signal influenced by the channel fading. For example, a degree of the channel fading is related to factors such as a length and a noise intensity of a channel (e.g., a wired/wireless channel). The equalizer module 1230 compensates the channel fading of the input signal DATA_IN. For example, the equalizer module 1230 modulates the input signal DATA_IN to generate and output the data signal DATA. For example, the equalizer module 1230 uses different parameters to modulate the input signal DATA_IN in order to output the data signal DATA having more preferable signal quality or having a waveform that is more suitable for analysis. For example, the equalizer module 1230 may include at least one of a continuous-time linear equalizer (CTLE), an infinite impulse response (IIR) circuit and a decision feedback equalizer (DFE), or equalizers of other types.

The algorithm circuit 1240 is coupled to the eye-width detection circuit 1210 and the equalizer module 1230. The algorithm circuit 1240 is configured to receive the eye-width information EW and output a parameter PARA to the equalizer module 1230. The equalizer module 1230 determines current parameters to be used according to the parameter PARA. For example, the eye-width detection circuit 1210 continuously detects the eye-width of the data signal DATA and outputs the corresponding eye-width information EW; the algorithm circuit 1240 continuously receives the eye-width information EW and generates different parameters PARA according to an algorithm; and according to the parameter PARA, the equalizer module 1230 continuously modulates the input signal DATA_IN to generate the data signals DATA having different eye-widths (or waveforms) until the algorithm circuit 1240 determines that an optimal parameter and a corresponding optimal eye-width (or optimal waveform) are obtained.

In summary, in an exemplary embodiment of the disclosure, the second clock signal having the clock signal consistent with the clock frequency of the first clock signal may be obtained first. After obtaining the second clock signal having the clock signal consistent with the clock frequency of the first clock signal, the second clock signal is delayed or accelerated by ¼ clock cycle and then the data signal is sampled by using the first clock signal and the adjusted second clock signal. Thereafter, the obtained sampling values may be adjusted by gradually moving the second clock signal close to the first clock signal until the obtained sampling value matches a specific condition. According to the sampling values matched to the condition, the eye-width of the data signal may be obtained and the corresponding eye-width information may be outputted. As a result, in comparison with the conventional method in which large amount of data is used for measuring the eye-width of data signal, the disclosure is capable of improving the efficiency of the eye-width detection.

It will be apparent to those skilled in the art that various modifications and variations may be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. An eye-width detector, comprising:
a phase interpolator, configured to receive a first clock signal and a phase control signal and output a second clock signal;
a calibration circuit, coupled to the phase interpolator, wherein the calibration circuit is configured to receive the first clock signal and the second clock signal and output a first control signal;
an eye-width detection circuit, coupled to the phase interpolator and the calibration circuit,
wherein the eye-width detection circuit is configured to receive a data signal, the first clock signal and the second clock signal and generate a first sampling value and a second sampling value,
wherein the eye-width detection circuit is further configured to output a second control signal if the first sampling value and the second sampling value do not match a first condition,
wherein the eye-width detection circuit is further configured to output eye-width information of the data signal if the first sampling value and the second sampling value match the first condition; and
a multiplexer, coupled to the phase interpolator, the calibration circuit and the eye-width detection circuit,
wherein the multiplexer is configured to receive the first control signal and the second control signal and output the phase control signal in response to a selection signal.

2. The eye-width detector according to claim 1, wherein the calibration circuit comprises:
a calibration state machine, coupled to the multiplexer,
wherein the calibration state machine is configured to determine whether a clock frequency of the first clock signal is consistent with a clock frequency of the second clock signal and output the first control signal if the clock frequency of the first clock signal is inconsistent with the clock frequency of the second clock signal.

3. The eye-width detector according to claim 2, wherein the calibration circuit further comprises:
a flip-flop circuit, coupled to the phase interpolator,
wherein the flip-flop circuit is configured to perform a sampling operation according to the first clock signal and the second clock signal;
a first latch circuit, coupled between the flip-flop circuit and the calibration state machine,
wherein the first latch circuit is configured to receive an output of the flip-flop circuit and output a first comparison signal,
wherein the calibration state machine determines whether the clock frequency of the first clock signal is consistent with the clock frequency of the second clock signal according to the first comparison signal.

4. The eye-width detector according to claim 2, wherein the calibration state machine is further configured to output a first phase reference value corresponding to the second clock signal if the clock frequency of the first clock signal is consistent with the clock frequency of the second clock signal.

5. The eye-width detector according to claim 1, wherein the eye-width detection circuit comprises:
an eye-width detection state machine, coupled to the calibration circuit,
wherein the eye-width detection state machine is configured to receive a first phase reference value from the calibration circuit and output a third control signal corresponding to the first phase reference value,
wherein the third control signal is configured to delay or accelerate the second clock signal by a default clock cycle,
wherein the multiplexer is further configured to receive the third control signal.

6. The eye-width detector according to claim 5, wherein the eye-width detection state machine is further configured to determine whether the first sampling value and the second sampling value match the first condition in correspondence to the third control signal being outputted.

7. The eye-width detector according to claim 6, wherein the eye-width detection state machine is further configured to obtain a second phase reference value of the second clock signal if the first sampling value and the second sampling value match the first condition,
wherein the eye-width detection circuit is further configured to output the eye-width information of the data signal according to the first phase reference value and the second phase reference value.

8. The eye-width detector according to claim 6, wherein the eye-width detection state machine determines whether the first sampling value and the second sampling value are equal, wherein the eye-width detection state machine determines that the first sampling value and the second sampling value do not match the first condition if the first sampling value and the second sampling value are not equal, wherein the eye-width detection state machine determines that the first sampling value and the second sampling value match the first condition if the first sampling value and the second sampling value are equal.

9. The eye-width detector according to claim 8, wherein the eye-width detection circuit further comprises:
an XOR circuit, coupled to the eye-width detection state machine,
wherein the XOR circuit is configured to perform an XOR operation according to the first sampling value and the second sampling value; and
a second latch circuit, coupled between the XOR circuit and the eye-width detection state machine,
wherein the second latch circuit is configured to receive an output of the XOR circuit and output a second comparison signal,
wherein the eye-width detection state machine determines whether the first sampling value and the second sampling value are equal according to the second comparison signal.

10. The eye-width detector according to claim 1, wherein the eye-width detection circuit comprises:
a first sampling circuit, coupled to the phase interpolator and configured to sample the data signal by using the first clock signal in order to output the first sampling value; and
a second sampling circuit, coupled to the phase interpolator,
wherein the second sampling circuit is configured to sample the data signal by using the second clock signal and output the second sampling value.

11. The eye-width detector according to claim 1, wherein the first clock signal is an output clock generated by a clock and data recovery circuit in correspondence to the data signal.

12. The eye-width detector according to claim 1, wherein the second control signal is configured to reduce a time difference between a first time-point and a second time-point,
wherein the first time-point is a sampling time corresponding to the first sampling value,
wherein the second time-point is a sampling time corresponding to the second sampling value.

13. A memory storage device, comprising:
a connection interface unit, configured to couple to a host system;
a rewritable non-volatile memory module; and
a memory control circuit unit, coupled to the connection interface unit and the rewritable non-volatile memory module,
wherein the connection interface unit comprises an eye-width detector,
wherein the eye-width detector comprises:
a phase interpolator, configured to receive a first clock signal and a phase control signal and output a second clock signal;
a calibration circuit, coupled to the phase interpolator, wherein the calibration circuit is configured to receive the first clock signal and the second clock signal and output a first control signal;
an eye-width detection circuit, coupled to the phase interpolator and the calibration circuit,
wherein the eye-width detection circuit is configured to receive a data signal, the first clock signal and the second clock signal and generate a first sampling value and a second sampling value,
wherein the eye-width detection circuit is further configured to output a second control signal if the first sampling value and the second sampling value do not match a first condition,
wherein the eye-width detection circuit is further configured to output eye-width information of the data signal if the first sampling value and the second sampling value match the first condition; and
a multiplexer, coupled to the phase interpolator, the calibration circuit and the eye-width detection circuit,
wherein the multiplexer is configured to receive the first control signal and the second control signal and output the phase control signal in response to a selection signal.

14. The memory storage device according to claim 13, wherein the calibration circuit comprises:
a calibration state machine, coupled to the multiplexer,
wherein the calibration state machine is configured to determine whether a clock frequency of the first clock signal is consistent with a clock frequency of the second clock signal and output the first control signal if the clock frequency of the first clock signal is inconsistent with the clock frequency of the second clock signal.

15. The memory storage device according to claim 14, wherein the calibration circuit further comprises:
a flip-flop circuit, coupled to the phase interpolator,
wherein the flip-flop circuit is configured to perform a sampling operation according to the first clock signal and the second clock signal;
a first latch circuit, coupled between the flip-flop circuit and the calibration state machine,
wherein the first latch circuit is configured to receive an output of the flip-flop circuit and output a first comparison signal,
wherein the calibration state machine determines whether the clock frequency of the first clock signal is consistent with the clock frequency of the second clock signal according to the first comparison signal.

16. The memory storage device according to claim 14, wherein the calibration state machine is further configured to output a first phase reference value corresponding to the second clock signal if the clock frequency of the first clock signal is consistent with the clock frequency of the second clock signal.

17. The memory storage device according to claim 13, wherein the eye-width detection circuit comprises:
an eye-width detection state machine, coupled to the calibration circuit,
wherein the eye-width detection state machine is configured to receive a first phase reference value from the calibration circuit and output a third control signal corresponding to the first phase reference value,
wherein the third control signal is configured to delay or accelerate the second clock signal by a default clock cycle,
wherein the multiplexer is further configured to receive the third control signal.

18. The memory storage device according to claim 17, wherein the eye-width detection state machine is further configured to determine whether the first sampling value and the second sampling value match the first condition in correspondence to the third control signal being outputted.

19. The memory storage device according to claim 18, wherein the eye-width detection state machine is further configured to obtain a second phase reference value of the second clock signal if the first sampling value and the second sampling value match the first condition,
  wherein the eye-width detection circuit is further configured to output the eye-width information of the data signal according to the first phase reference value and the second phase reference value.

20. The memory storage device according to claim 18, wherein the eye-width detection state machine determines whether the first sampling value and the second sampling value are equal,
  wherein the eye-width detection state machine determines that the first sampling value and the second sampling value do not match the first condition if the first sampling value and the second sampling value are not equal,
  wherein the eye-width detection state machine determines that the first sampling value and the second sampling value match the first condition if the first sampling value and the second sampling value are equal.

21. The memory storage device according to claim 20, wherein the eye-width detection circuit further comprises:
  an XOR circuit, coupled to the eye-width detection state machine,
  wherein the XOR circuit is configured to perform an XOR operation according to the first sampling value and the second sampling value; and
  a second latch circuit, coupled between the XOR circuit and the eye-width detection state machine,
  wherein the second latch circuit is configured to receive an output of the XOR circuit and output a second comparison signal,
  wherein the eye-width detection state machine determines whether the first sampling value and the second sampling value are equal according to the second comparison signal.

22. The memory storage device according to claim 13, wherein the eye-width detection circuit comprises:
  a first sampling circuit, configured to sample the data signal by using the first clock signal in order to output the first sampling value; and
  a second sampling circuit, coupled to the phase interpolator,
  wherein the second sampling circuit is configured to sample the data signal by using the second clock signal in order to output the second sampling value.

23. The memory storage device according to claim 13, wherein the connection interface unit further comprises:
  a clock and data recovery circuit, coupled to the eye-width detector,
  wherein the clock and data recovery circuit is configured to receive the data signal and generate an output clock in correspondence to the data signal,
  wherein the output clock is the first clock signal.

24. The memory storage device according to claim 13, wherein the connection interface unit further comprises:
  an algorithm circuit, coupled to the eye-width detector,
  wherein the algorithm circuit is configured to receive the eye-width information of the data signal and output a parameter; and
  an equalizer module, coupled to the eye-width detector and the algorithm circuit,
  wherein the equalizer module is configured to receive an input signal and the parameter and modulate the input signal according to the parameter in order to output the data signal.

25. An eye-width detection method of data signal, performed by a memory storage device, the eye-width detection method of data signal comprising:
  receiving a first clock signal and a phase control signal and outputting a second clock signal by a connection interface unit of the memory storage device;
  receiving the first clock signal and the second clock signal and outputting a first control signal by the connection interface unit;
  receiving a data signal, the first clock signal and the second clock signal and generating a first sampling value and a second sampling value by the connection interface unit;
  outputting a second control signal if the first sampling value and the second sampling value do not match a first condition by the connection interface unit;
  outputting eye-width information of the data signal by the connection interface unit if the first sampling value and the second sampling value match the first condition; and
  receiving the first control signal and the second control signal and outputting the phase control signal in response to a selection signal by the connection interface unit.

26. The eye-width detection method of data signal according to claim 25, further comprising:
  determining whether a clock frequency of the first clock signal is consistent with a clock frequency of the second clock signal,
  wherein the step of outputting the first control signal is performed when determining that the clock frequency of the first clock signal is inconsistent with the clock frequency of the second clock signal.

27. The eye-width detection method of data signal according to claim 26, wherein the step of determining whether the clock frequency of the first clock signal is consistent with the clock frequency of the second clock signal comprises:
  performing a sampling operation according to the first clock signal and the second clock signal;
  receiving an output of the sampling operation and outputting a first comparison signal; and
  determining whether the clock frequency of the first clock signal is consistent with the clock frequency of the second clock signal according to the first comparison signal.

28. The eye-width detection method of data signal according to claim 26, further comprising:
  outputting a first phase reference value corresponding to the second clock signal if the clock frequency of the first clock signal is consistent with the clock frequency of the second clock signal.

29. The eye-width detection method of data signal according to claim 25, further comprising:
  receiving a first phase reference value and outputting a third control signal corresponding to the first phase reference value,
  wherein the third control signal is configured to delay or accelerate the second clock signal by a default clock cycle,
  wherein the step of receiving the first control signal and the second control signal further comprises:
    receiving the third control signal.

30. The eye-width detection method of data signal according to claim 29, further comprising:
determining whether the first sampling value and the second sampling value match the first condition in correspondence to the third control signal being outputted.

31. The eye-width detection method of data signal according to claim 30, further comprising:
obtaining a second phase reference value of the second clock signal if the first sampling value and the second sampling value match the first condition,
wherein the step of outputting the eye-width information of the data signal comprises:
outputting the eye-width information of the data signal according to the first phase reference value and the second phase reference value.

32. The eye-width detection method of data signal according to claim 30, wherein the step of determining whether the first sampling value and the second sampling value match the first condition comprises:
determining whether the first sampling value and the second sampling value are equal;
determining that the first sampling value and the second sampling value do not match the first condition if the first sampling value and the second sampling value are not equal; and
determining that the first sampling value and the second sampling value match the first condition if the first sampling value and the second sampling value are equal.

33. The eye-width detection method of data signal according to claim 32, wherein the step of determining whether the first sampling value and the second sampling value are equal comprises:
performing an XOR operation according to the first sampling value and the second sampling value;
receiving an output of the XOR operation and outputting a second comparison signal; and
determining whether the first sampling value and the second sampling value are equal according to the second comparison signal.

34. The eye-width detection method of data signal according to claim 25, further comprising:
sampling the data signal by using the first clock signal in order to output the first sampling value; and
sampling the data signal by using the second clock signal in order to output the second sampling value.

35. The eye-width detection method of data signal according to claim 25, wherein the first clock signal is an output clock generated by a clock and data recovery circuit in correspondence to the data signal.

* * * * *